(12) United States Patent
Bruchman et al.

(10) Patent No.: US 10,376,360 B2
(45) Date of Patent: Aug. 13, 2019

(54) MULTI-FRAME PROSTHETIC VALVE APPARATUS AND METHODS

(71) Applicant: W. L. Gore & Associates, Inc., Newark, DE (US)

(72) Inventors: William C. Bruchman, Camp Verde, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/797,526

(22) Filed: Mar. 12, 2013

(65) Prior Publication Data

US 2014/0031927 A1     Jan. 30, 2014

Related U.S. Application Data

(60) Provisional application No. 61/676,812, filed on Jul. 27, 2012.

(51) Int. Cl.
*A61F 2/24* (2006.01)

(52) U.S. Cl.
CPC .......... *A61F 2/2415* (2013.01); *A61F 2/2418* (2013.01); *A61F 2210/0076* (2013.01); *A61F 2220/005* (2013.01); *A61F 2230/0054* (2013.01)

(58) Field of Classification Search
CPC .... A61F 2/2475; A61F 2/2418; A61F 2/2412; A61F 2/2415; A61F 2/2409; A61F 2/24;
(Continued)

(56) References Cited

U.S. PATENT DOCUMENTS 3,953,566 A    4/1976  Gore
4,178,639 A    12/1979 Bokros
(Continued)

FOREIGN PATENT DOCUMENTS

CN    102764169 A    11/2012
EP     2359774 B1     8/2011
(Continued)

OTHER PUBLICATIONS

International Search Report for PCT/US2013/046389 mailed Jan. 21, 2014, corresponding to U.S. Appl. No. 13/797,633; 7 pages.
(Continued)

*Primary Examiner* — David J Isabella

(57) ABSTRACT

Described embodiments are directed toward centrally-opening leaflet prosthetic valve devices having two frames. A leaflet frame is coaxially disposed within a body frame. The body frame has a tubular shape defining a body frame lumen. The leaflet frame has an annular shape defining a plurality of U-shaped portions each defining a base and a plurality of posts. The leaflet frame is located coaxial with and at least substantially within the body frame lumen. A first film is coupled to the body frame and a second film is coupled to and extends across each of the U-shaped portions defining a leaflet having a free edge. At least one of the first film and second film couples the body frame to the leaflet frame. The leaflets are moveable between an open and closed position with the leaflet free edge of each of the leaflets abutting an adjacent leaflet free edge when in the closed position.

20 Claims, 10 Drawing Sheets

(58) Field of Classification Search
CPC ........ A61F 2220/005; A61F 2210/0076; A61F 2230/0054
USPC ......... 623/1.24, 1.26, 2.12, 2.14, 2.15, 2.17, 623/2.18, 2.19, 2.42, 2.1, 2.11, 2.13, 2.16
See application file for complete search history.

(56) References Cited

U.S. PATENT DOCUMENTS

| | | | |
|---|---|---|---|
| 4,265,694 | A | 5/1981 | Boretos et al. |
| 4,477,930 | A | 10/1984 | Totten et al. |
| 5,628,791 | A | 5/1997 | Bokros et al. |
| 5,708,044 | A | 1/1998 | Branca |
| 6,174,331 | B1 | 1/2001 | Moe et al. |
| 6,283,994 | B1 | 9/2001 | Moe et al. |
| 6,283,995 | B1 | 9/2001 | Moe et al. |
| 6,287,334 | B1 | 9/2001 | Moll et al. |
| 6,328,763 | B1 | 12/2001 | Love et al. |
| 6,454,798 | B1 | 9/2002 | Moe |
| 6,482,228 | B1 | 11/2002 | Norred |
| 6,541,589 | B1 | 4/2003 | Baillie |
| 6,562,069 | B2 | 5/2003 | Cai et al. |
| 6,613,086 | B1 | 9/2003 | Moe et al. |
| 6,666,885 | B2 | 12/2003 | Moe |
| 6,916,338 | B2 | 7/2005 | Speziali |
| 6,953,332 | B1 | 10/2005 | Kurk et al. |
| 7,306,729 | B2 | 12/2007 | Bacino et al. |
| 7,381,218 | B2 * | 6/2008 | Schreck .......... 623/1.26 |
| 7,462,675 | B2 * | 12/2008 | Chang et al. ............ 526/247 |
| 7,510,575 | B2 | 3/2009 | Spenser et al. |
| 7,531,611 | B2 | 5/2009 | Sabol et al. |
| 7,708,775 | B2 | 5/2010 | Rowe et al. |
| 7,780,725 | B2 | 8/2010 | Haug et al. |
| 7,967,853 | B2 | 6/2011 | Eidenschink et al. |
| 7,993,394 | B2 | 8/2011 | Hariton et al. |
| 8,637,144 | B2 | 1/2014 | Ford |
| 8,728,154 | B2 | 5/2014 | Alkhatib |
| 8,870,948 | B1 * | 10/2014 | Erzberger et al. .......... 623/2.1 |
| 8,961,599 | B2 | 2/2015 | Bruchman et al. |
| 9,101,469 | B2 | 8/2015 | Bruchman et al. |
| 9,139,669 | B2 | 9/2015 | Xu et al. |
| 9,144,492 | B2 | 9/2015 | Bruchman et al. |
| 9,283,072 | B2 | 3/2016 | Bruchman |
| 9,398,952 | B2 | 7/2016 | Bruchman et al. |
| 9,737,398 | B2 | 8/2017 | Bruchman et al. |
| 9,743,932 | B2 | 8/2017 | Amplatz et al. |
| 9,968,443 | B2 | 5/2018 | Bruchman et al. |
| 2002/0082687 | A1 | 6/2002 | Moe |
| 2003/0114913 | A1 | 6/2003 | Spenser et al. |
| 2004/0024448 | A1 * | 2/2004 | Chang et al. .......... 623/1.42 |
| 2004/0024451 | A1 | 2/2004 | Johnson |
| 2004/0039436 | A1 | 2/2004 | Spenser et al. |
| 2004/0243222 | A1 | 12/2004 | Osborne et al. |
| 2005/0027348 | A1 | 2/2005 | Case et al. |
| 2005/0137682 | A1 | 6/2005 | Justino |
| 2006/0122693 | A1 | 6/2006 | Biadillah et al. |
| 2006/0290027 | A1 | 12/2006 | O'Connor et al. |
| 2007/0010876 | A1 | 1/2007 | Salahieh et al. |
| 2007/0021826 | A1 * | 1/2007 | Case et al. ............ 623/1.15 |
| 2007/0207186 | A1 | 9/2007 | Scanlon et al. |
| 2008/0009940 | A1 | 1/2008 | Cribier |
| 2008/0065198 | A1 | 3/2008 | Quintessenza |
| 2008/0133004 | A1 | 6/2008 | White |
| 2008/0195199 | A1 | 8/2008 | Kheradvar et al. |
| 2008/0220041 | A1 | 9/2008 | Brito et al. |
| 2009/0157175 | A1 | 6/2009 | Benichou |
| 2009/0240320 | A1 | 9/2009 | Tuval et al. |
| 2009/0264997 | A1 | 10/2009 | Salahieh et al. |
| 2010/0036021 | A1 * | 2/2010 | Lee et al. .......... 523/322 |
| 2010/0082094 | A1 | 4/2010 | Quadri et al. |
| 2010/0137998 | A1 * | 6/2010 | Sobrino-Serrano et al. .......... 623/23.68 |
| 2010/0145438 | A1 | 6/2010 | Barone |
| 2010/0168839 | A1 | 7/2010 | Braido et al. |
| 2010/0185274 | A1 * | 7/2010 | Moaddeb et al. .......... 623/1.24 |
| 2010/0191320 | A1 | 7/2010 | Straubinger et al. |
| 2010/0204781 | A1 | 8/2010 | Alkhatib |
| 2010/0204785 | A1 | 8/2010 | Alkhatib |
| 2010/0217382 | A1 | 8/2010 | Chau et al. |
| 2010/0262231 | A1 | 10/2010 | Tuval et al. |
| 2011/0054515 | A1 | 3/2011 | Bridgeman et al. |
| 2011/0208283 | A1 | 8/2011 | Rust |
| 2011/0218619 | A1 * | 9/2011 | Benichou et al. .......... 623/2.11 |
| 2011/0251678 | A1 | 10/2011 | Eidenschink et al. |
| 2011/0257739 | A1 | 10/2011 | Corbett |
| 2012/0078357 | A1 | 3/2012 | Conklin |
| 2012/0083839 | A1 | 4/2012 | Letac et al. |
| 2012/0101567 | A1 | 4/2012 | Jansen |
| 2012/0101571 | A1 | 4/2012 | Thambar et al. |
| 2012/0130471 | A1 | 5/2012 | Shoemaker et al. |
| 2012/0185038 | A1 | 7/2012 | Fish et al. |
| 2012/0323315 | A1 | 12/2012 | Bruchman et al. |
| 2014/0031924 | A1 | 1/2014 | Bruchman et al. |
| 2014/0031927 | A1 | 1/2014 | Bruchman et al. |
| 2014/0172078 | A1 | 6/2014 | Bruchman et al. |
| 2014/0172083 | A1 | 6/2014 | Bruchman et al. |
| 2014/0180400 | A1 | 6/2014 | Bruchman et al. |
| 2014/0236289 | A1 | 8/2014 | Alkhatib |
| 2014/0324164 | A1 | 10/2014 | Gross |
| 2015/0142100 | A1 * | 5/2015 | Morriss .......... A61F 2/2418 623/2.4 |
| 2016/0157998 | A1 | 6/2016 | Bruchman |
| 2016/0213465 | A1 | 7/2016 | Girard |
| 2017/0095330 | A1 | 4/2017 | Malewicz |

FOREIGN PATENT DOCUMENTS

| | | |
|---|---|---|
| FR | 2 591 100 | 6/1987 |
| GB | 2 312 485 | 10/1997 |
| JP | 196932400 B | 12/1969 |
| JP | 2012152563 A | 8/2012 |
| NO | 2012040643 A2 | 3/2012 |
| WO | 1996002212 A1 | 2/1996 |
| WO | 00/62716 | 10/2000 |
| WO | 2006108090 A2 | 10/2006 |
| WO | 2008/097592 | 8/2008 |
| WO | WO2009029199 A1 | 3/2009 |
| WO | WO 2010057262 A1 * | 5/2010 |
| WO | 2011/109450 | 9/2011 |
| WO | 2011/109801 | 9/2011 |
| WO | 2011112706 A2 | 9/2011 |
| WO | 2012/082952 | 6/2012 |
| WO | 2012/110767 | 8/2012 |
| WO | 2012/167131 | 12/2012 |
| WO | 2014/018432 | 1/2014 |
| WO | 2014144937 A2 | 9/2014 |
| WO | 2016186909 A1 | 11/2016 |

OTHER PUBLICATIONS

International Search Report for PCT/US2013/051431 mailed Jan. 20, 2014, corresponding to U.S. Appl. No. 13/797,526; 6 pages.
International Search Report for PCT/US2013/076688 mailed Feb. 27, 2014, corresponding to U.S. Appl. No. 14/133,563, 5 pages.
International Search Report for PCT/US2013/074962 mailed Feb. 27, 2014, corresponding to U.S. Appl. No. 13/833,650, 4 pages.
International Search Report for PCT/US2013/068390 mailed Apr. 29, 2014, corresponding to U.S. Appl. No. 13/835,988, 7 pages.
International Search Report for PCT/US2013/076504 mailed Apr. 28, 2014, corresponding to U.S. Appl. No. 14/133,491, 7 pages.
International Search Report for PCT/US2013/071632 mailed Apr. 28, 2014, corresponding to U.S. Appl. No. 13/841,334, 6 pages.
International Search Report for PCT/US2013/075274 mailed Feb. 27, 2014, corresponding to U.S. Appl. No. 13/843,196, 5 pages.
International Search Report for PCT/US2013/075380 mailed Mar. 6, 2014, corresponding to U.S. Appl. No. 13/869,524, 5 pages.
International Search Report for PCT/US2013/068780 mailed Feb. 27, 2014, corresponding to U.S. Appl. No. 13/869,878, 4 pages.
Clough, Norman E. Introducing a New Family of GORE™ ePTFE Fibers (2007).
European Search Report from EP16196687.4, dated Nov. 21, 2017, 5 pages.

(56) References Cited

OTHER PUBLICATIONS

International Search Report and Written Opinion from PCT/US2018/050766, dated Mar. 11, 2019, 16 pages.

* cited by examiner

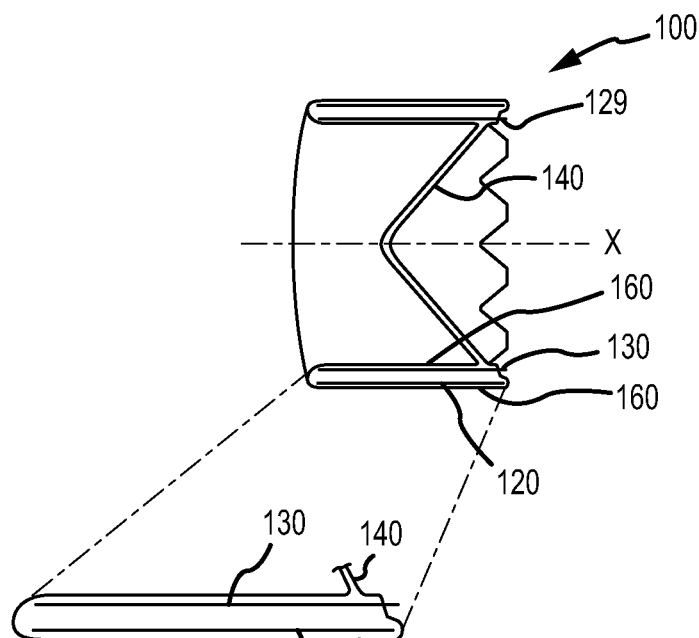
FIG.3A
FIG.3B
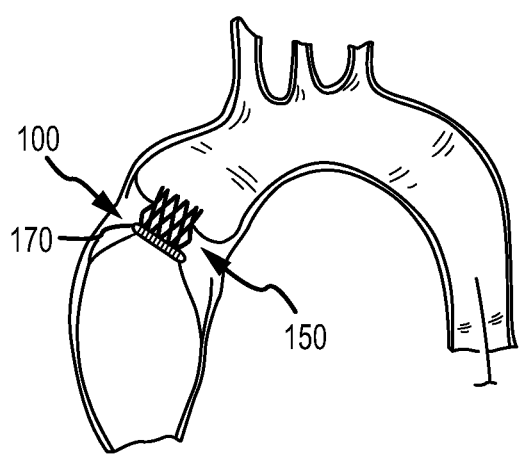
FIG.4

 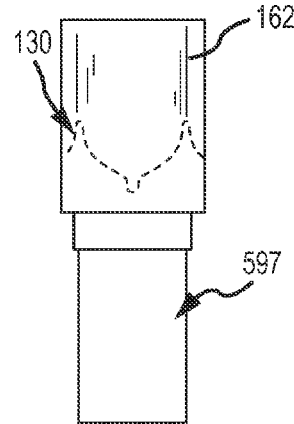 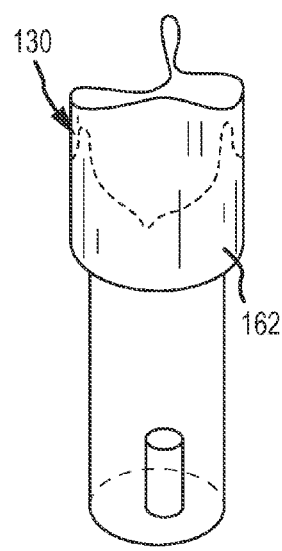 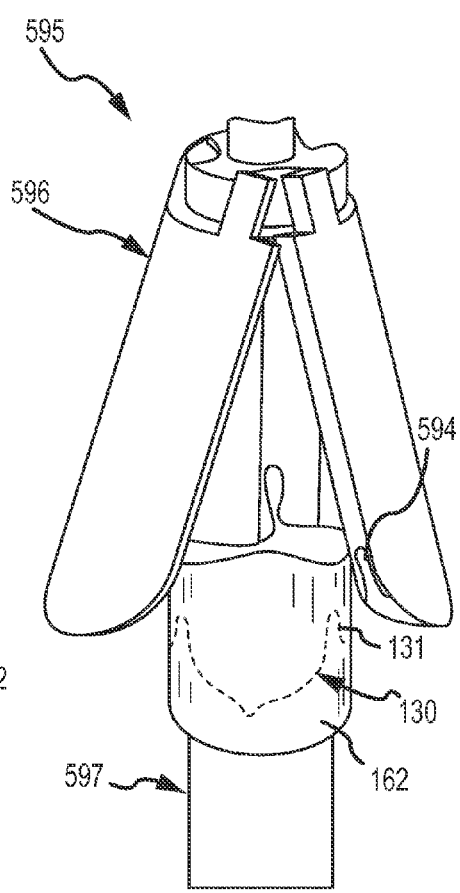
FIG.6C  FIG.6D  FIG.6E

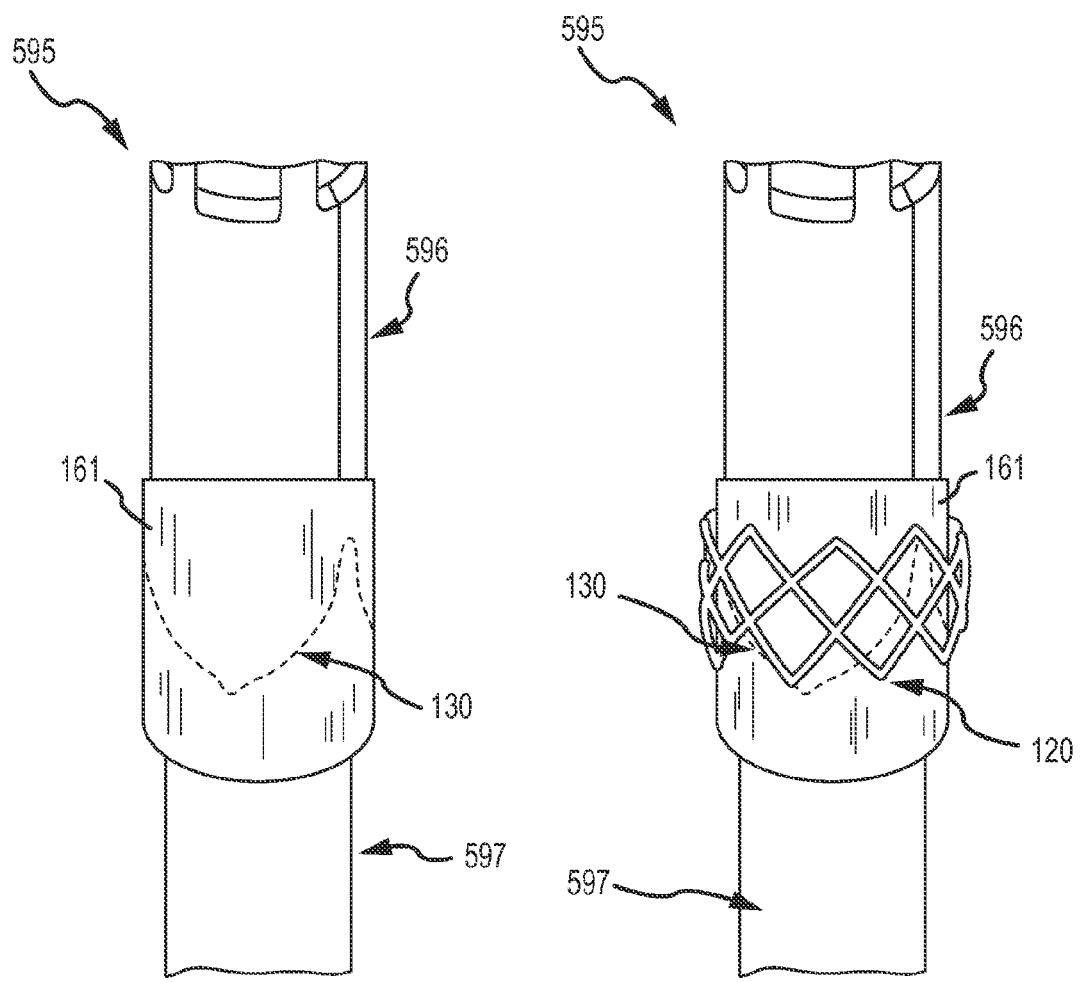

MULTI-FRAME PROSTHETIC VALVE APPARATUS AND METHODS

CROSS-REFERENCE TO RELATED APPLICATIONS

This application is claims priority to provisional application Ser. No. 61/676,812 filed Jul. 27, 2012, which is herein incorporated by reference in its entirety.

FIELD

The present disclosure relates generally to prosthetic valves and more specifically synthetic flexible leaflet-type prosthetic valve devices, systems, and methods for implantation.

BACKGROUND

Bioprosthetic valves have been developed that attempt to mimic the function and performance of a native valve. Flexible leaflets are fabricated from biological tissue such as bovine pericardium. In some valve designs the biological tissue is sewn onto a relatively rigid frame that supports the leaflets and provides dimensional stability when implanted. Although bioprosthetic valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic valve, herein referred to as a synthetic leaflet valve (SLV). However, synthetic leaflet valves have not become a valid valve replacement option since they suffer premature failure, due to, among other things, suboptimal design and lack of a durable synthetic material.

A number of fabrication techniques have been used to couple the leaflets to a frame, including sewing individual leaflets to the frame (biological and synthetic), and for synthetic leaflets only, injection molding and dip coating a polymer onto the frame. In many cases, the resulting leaflet is supported on the frame and defines a flap having a mounting edge where the leaflet is coupled to the frame and a free edge that allows the flap to move. The flap moves under the influence of fluid pressure. In operation, the leaflets open when the upstream fluid pressure exceeds the downstream fluid pressure and close when the downstream fluid pressure exceeds the upstream fluid pressure. The free edges of the leaflets coapt under the influence of downstream fluid pressure closing the valve to prevent downstream blood from flowing retrograde through the valve.

Valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material. Mechanical failure at the mounting edge is especially prevalent with synthetic leaflets.

There remains a need for a more durable flexible leaflet prosthetic valve.

SUMMARY

Described embodiments are directed to apparatus, system, and methods for valve replacement, such as cardiac valve replacement. More specifically, described embodiments are directed toward flexible leaflet valve devices having biological or synthetic leaflet material and a multi-part support member or frame, and methods of making and implanting the valve devices.

According to an embodiment, a valve comprises a leaflet frame, a body frame and any number of leaflets suitable for the size and function of the valve. According to another embodiment, a method of making the valve comprises the steps of fitting the leaflet frame and body frame with a biocompatible material as described herein, and thereby also forming leaflets.

According to an embodiment, a valve comprises a body frame defining a generally tubular shape defining a body frame lumen, a leaflet frame having a generally annular shape defining a plurality of U-shaped portions each defining a base and a plurality of posts, the leaflet frame being located coaxial with and at least substantially within the body frame lumen, a first film coupled to the body frame, and a second film coupled to and extending across each of the U-shaped portions defining a leaflet, each leaflet having a leaflet free edge, at least one of the first film and second film at least partially coupling the body frame to the leaflet frame, wherein the leaflet free edges are operable to abut adjacent leaflet free edges and are moveable between an open and closed position.

In accordance with a method of making a multi-frame prosthetic valve comprising: providing a body frame defining a generally tubular shape defining a body frame lumen; providing a leaflet frame having a generally annular shape defining a plurality of U-shaped portions each defining a base and a plurality of posts; providing a film; forming a first layer of the film into a tubular form; coaxially placing the leaflet frame over the tubular form of the first layer of film; wrapping the film around the leaflet frame and the tubular form of the first layer of film, the film extending across each of the U-shaped portions so as to define a leaflet therein; bonding the first layer and the second layer to each other and the leaflet frame; clamping the leaflets disposed in the U-shaped portions to enclose the leaflets; forming a third layer of the film over the leaflet frame; placing the body frame over the third layer of the film and over the leaflet frame such that the leaflet frame is coaxially disposed within the body frame lumen forming a fourth layer of the film over the body frame and the third layer of the film; and bonding the third layer and the fourth layer to each other and the body frame.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIGS. 3A and 3B are a side cross-sectional view and detail view, respectively, of an embodiment of a valve;

FIG. 4 is a side view of an embodiment of a valve within anatomy in accordance with an embodiment;

FIGS. 6A-6H are various side and perspective views of an embodiment of assembling a valve.

DETAILED DESCRIPTION

Figure 1A:
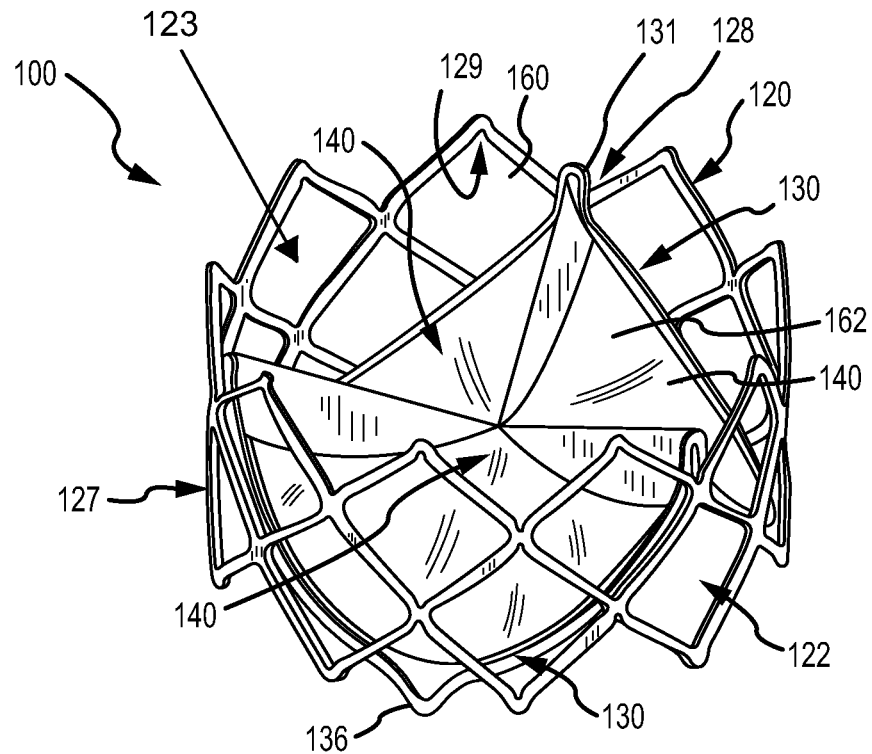
FIG. 1A is a perspective view of an embodiment of a valve comprising a leaflet frame and a body frame.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a flexible component of a one-way valve wherein the leaflet is operable to move between an open and closed position under the influence of a pressure differential. In an open position, the leaflet allows blood to flow through the valve. In a closed potion, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets opens and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer can be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to any material with biocompatible characteristics including synthetic, such as, but not limited to, a biocompatible polymer, or a biological material, such as, but not limited to, bovine pericardium. Biocompatible material may comprise a first film and a second film as described herein for various embodiments.

The terms native valve orifice and tissue orifice refer to an anatomical structure into which a prosthetic valve can be placed. Such anatomical structure includes, but is not limited to, a location wherein a cardiac valve may or may not have been surgically removed. It is understood that other anatomical structures that can receive a prosthetic valve include, but are not limited to, veins, arteries, ducts and shunts. It is further understood that a valve orifice or implant site may also refer to a location in a synthetic or biological conduit that may receive a valve.

As used herein, "couple" means to join, couple, connect, attach, adhere, affix, or bond, whether directly or indirectly, and whether permanently or temporarily.

Embodiments herein include various apparatus, systems, and methods for a prosthetic valve, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

In accordance with embodiments, the valve has leaflets that are supported by a leaflet frame that is coaxial with and at least partially nested within a body frame. Each of the body frame and leaflet frame may have different physical properties suitable for a particular purpose. In accordance with embodiments, the body frame may be relatively stiff so as to abut and fixedly engage the tissue orifice as well as provide dimensional stability to the valve. The leaflet frame may be relatively less stiff relative to the body frame. The benefit of the leaflet frame being relatively less stiff relative to the body frame may be to slow down the rate of loading on the leaflets to reduce the stress levels on the leaflets whereby improving valve durability. Stiff and stiffness, as used herein and as is commonly used in engineering, is a measure of the resistance to deformation given by a body. Stiff and stiffness is a function of, among other things, material properties, the shape of the object, and the boundary conditions on the object. Stiffness of the leaflet frame 130 (see FIG. 1A) may be measured by any number of methods known in the art. In accordance with one method, cables may be coupled to each of the three posts 131 and brought together so as to allow the cables to be pulled simultaneously along the axis of the leaflet frame, with the leaflet frame restrained about the flex points 136 or as held by the body frame 120. The amount of force on the cables required to deflect the three posts toward the axis provides a measure of stiffness. The same may be done with the body frame 120 with the cables coupled to three equally spaced points on the body frame 120, such as an apex of the diamond-shaped apertures 122 opposite from the flex points 136.

The Valve

Figure 1B:
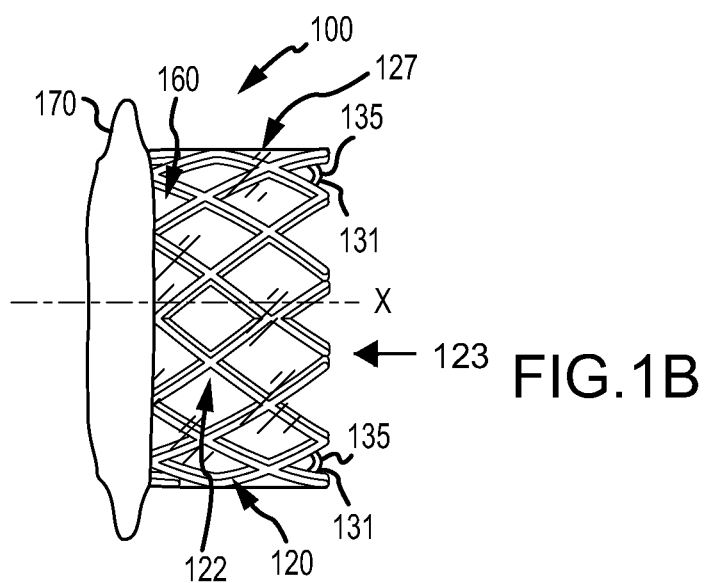
FIG. 1B is a side view of the embodiment of the valve of FIG. 1A.
Figure 1C:
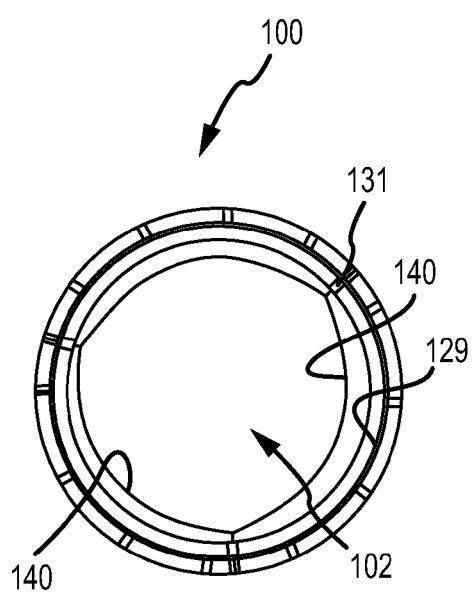
FIG. 1C is an axial view of the embodiment of the valve of FIG. 1A in an open configuration.
Figure 1D:
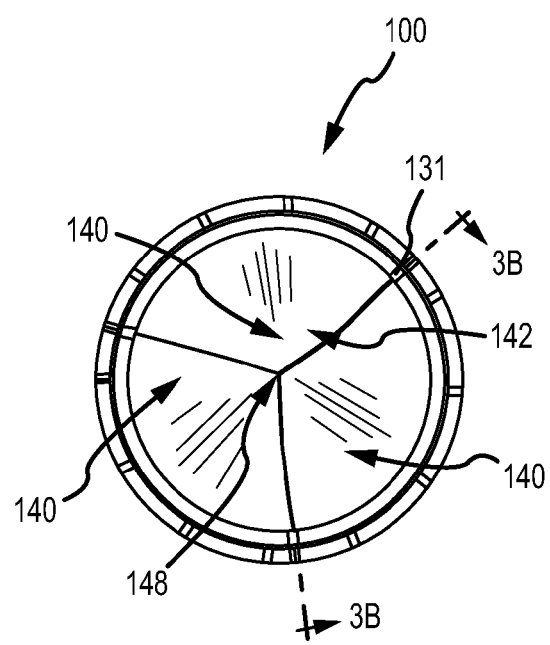
FIG. 1D is an axial view of the embodiment of the valve of FIG. 1A in a closed configuration.
Figure 2A:
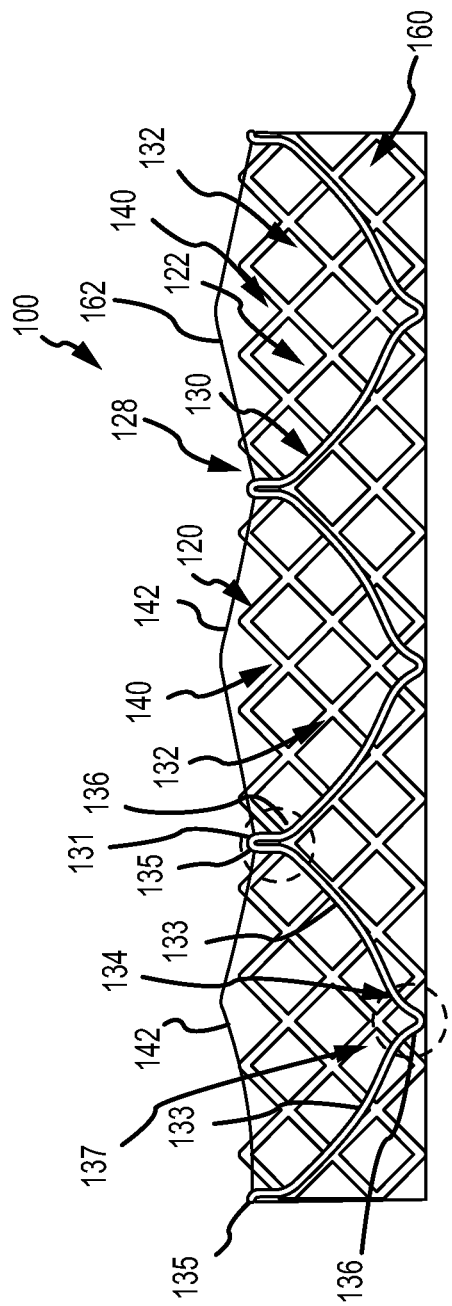
FIG. 2A is a representation of the embodiment of the valve of FIG. 1A unrolled to a flat orientation.
Figure 2B:
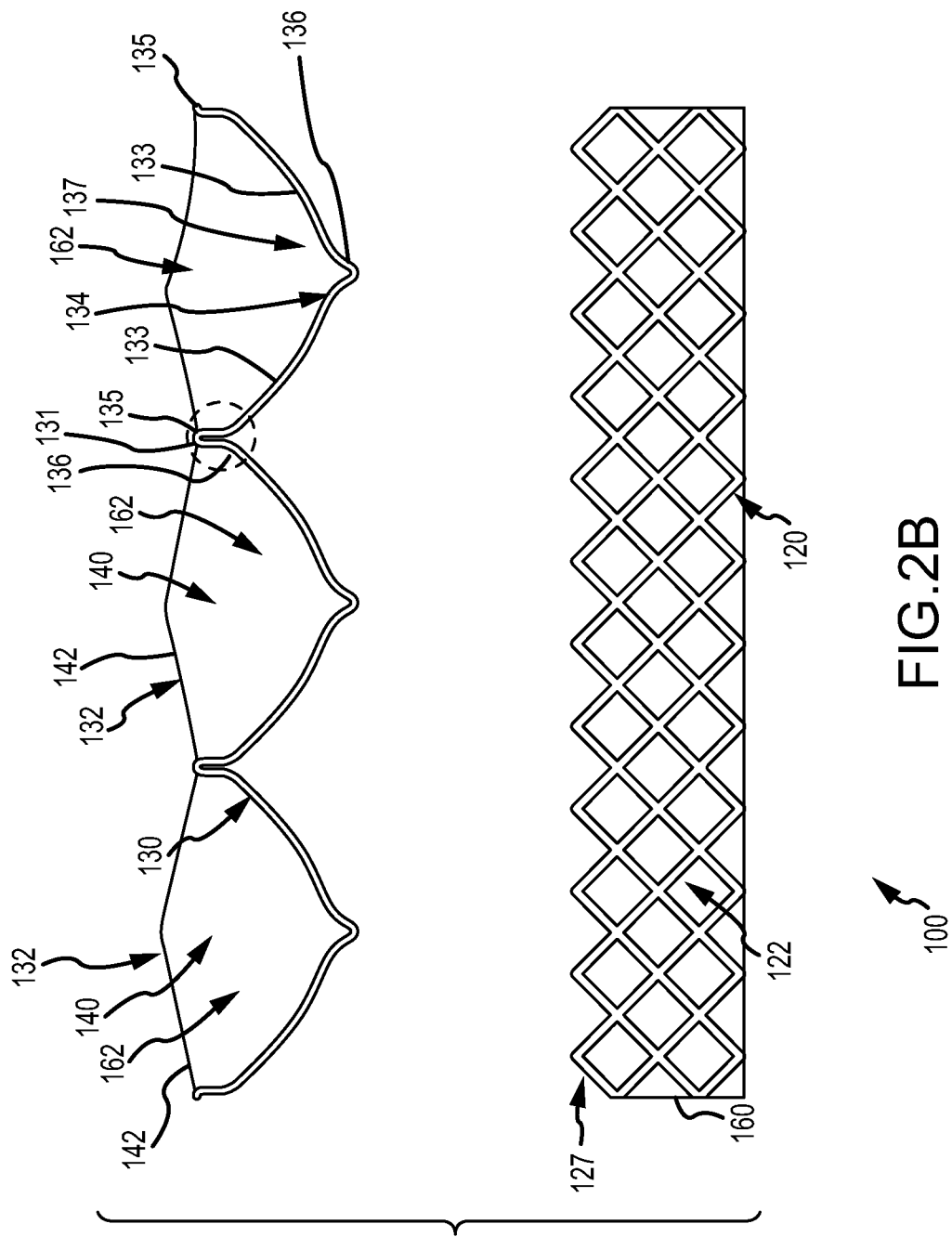
FIG. 2B is an exploded view of a representation of the embodiment of the valve of FIG. 1A unrolled to a flat orientation.

FIGS. 1A and 1B are perspective and side views, respectively, of a valve 100, in accordance with an embodiment. FIGS. 1C and 1D are axial views of the valve 100 in an open and closed configuration, respectively. FIG. 2A illustrates the embodiment of FIG. 1A wherein the valve 100 has been longitudinally cut and laid open to better illustrate the elements of the generally tubular-shaped valve 100. FIG. 2B illustrates the embodiment of FIG. 1A wherein the valve 100 has been longitudinally cut and laid open, and partially exploded so as to better illustrate the elements of the generally tubular-shaped valve 100.

The valve 100 comprises a body frame 120, a leaflet frame 130, and a first film 160 covering the body frame 120 and a second film 162 covering the leaflet frame 130 and forming leaflets 140.

The Film

A film 160 is generally any sheet-like, biocompatible material configured to couple to the body frame 120 and the leaflet frame 130. The leaflets 140 can also be comprised of the film 160. In an embodiment, the film 160 can be formed from a generally tubular material to couple the body frame 120 and the leaflet frame 130, and to form the leaflets 140.

It is understood that the film 160 is used generically for one or more biocompatible materials suitable for a particular purpose. It is also understood that the film coupled to the body frame 120 may not be the same film coupled to the leaflet frame 130, or the same film serving as leaflets 140, although in some embodiments the same film is coupled to the body frame 120 and the leaflet frame 130 and defines leaflets 140.

The film 160 can comprise one or more of the membrane, composite material, or laminate. Details of various types of film 160 are discussed below.

The Body Frame

The body frame 120 is a generally tubular member defining a body frame lumen 123 having a body frame inner surface 129, as shown in FIGS. 1A, 1B. The body frame 120 defines a valve orifice 102. The body frame 120 provides structural, load-bearing support to the leaflet frame 130. In addition, the body frame 120 can be configured to provide positive engagement to the recipient tissue at the implantation site.

The body frame 120 can comprise any metallic or polymeric material that is generally biocompatible. For example, the body frame 120 can comprise a material, such as, but not limited to nitinol, cobalt-nickel alloy, stainless steel, and polypropylene, acetyl homopolymer, acetyl copolymer, ePTFE, other alloys or polymers, or any other biocompatible material having adequate physical and mechanical properties to function as described herein.

By way of example, and as illustrated in the embodiments of FIGS. 1A-1D and 2A-2B, the valve 100 includes the body frame 120 that defines a stent having apertures 122. The open framework of the stent can define any number of features, repeatable or otherwise, such as geometric shapes and/or linear or meandering series of sinusoids. An open framework can be etched, cut, laser cut, or stamped into a tube or a sheet of material, with the sheet then formed into a substantially cylindrical structure. In other embodiments, the body frame 120 can have a solid wall. Alternatively, an elongated material, such as a wire, bendable strip, or a series thereof, can be bent or braided and formed into a substantially cylindrical structure. For example, body frame 120 can comprise a stent or stent graft type structure or a conventional sewing frame.

In accordance with embodiments, the body frame 120 can be configured to provide positive engagement to an implant site. In an embodiment, the valve 100 further includes a sewing cuff 170 coupled about the body frame 120, as shown in FIG. 1B, that is operable to accept suture so as to be sewn to a tissue orifice 150, for example, to maintain position, as shown in FIG. 4. In another embodiment, the body frame 120 can comprise one or more anchors (not shown) configured to engage the implant site, such as the tissue orifice 150 to secure the valve 100. In other embodiments, the body frame 120 can be otherwise secured to the implant site. It is understood that conventional, surgical techniques to implant prosthetic valves can be used to implant the valve 100, in accordance with embodiments. It is understood that valves in accordance with some embodiments may be implanted using intravascular techniques.

It is appreciated that other elements or means for coupling the valve 100 to an implant site are anticipated. By way of example, but not limited thereto, other means, such as mechanical and adhesive means may be used to couple the valve 100 to a synthetic or biological conduit.

Leaflet Frame

The leaflet frame 130 comprises a generally annular member defining a predetermined repeating pattern as shown in FIGS. 1A and 2A-2B. The leaflet frame 130 can comprise a wire, ribbon, cut tube, or any other element suitable for the particular purpose. As shown in FIGS. 2A-2B, the leaflet frame 130 comprises three interconnected U-shaped portions 132. Each of the U-shaped portions 132 defines two sides 133 that define a base 134, with each side 133 having a free end 135. In this embodiment, the base 134 defines a flex point 136 which will be described further below. The free end 135 of one U-shaped portion 132 is interconnected with a free end 135 of an adjacent U-shaped portion 132 which define a post 131.

A relatively less stiff leaflet frame 130 supporting the leaflets 140 can be more likely to reduce the loading encountered by the opening and closing leaflets 140 as compared to a more stiff leaflet frame 130. The leaflet frame 130 having a relatively less stiff property may reduce leaflet accelerations and reduce the closing stresses on the leaflets 140. In addition, the leaflet frame 130 can be elastically deformable so as to allow the leaflet frame 130 to flex and thus to facilitate surgical placement.

The leaflet frame 130 can comprise, such as, but not limited to, any elastically deformable metallic or polymeric material that is generally biocompatible. The leaflet frame 130 can comprise a shape-memory material, such as nitinol, a nickel-titanium alloy. Other materials suitable for the leaflet frame 130 include, but not limited to, other titanium alloys, stainless steel, cobalt-nickel alloy, polypropylene, acetyl homopolymer, acetyl copolymer, other alloys or polymers, or any other material that is generally biocompatible having adequate physical and mechanical properties to function as a leaflet frame 130 as described herein.

In accordance with an embodiment, the leaflet frame 130 comprises a shape memory material operable to flex under load and retain its original shape when the load is removed. The leaflet frame 130 and the body frame 120 can comprise the same or different materials.

Leaflet

Each of the U-shaped portions 132 of the leaflet frame 130 defines an inner region 137. Each inner region 137 is provided with a biocompatible material, such as the second film 162 which can be coupled to the sides 133 and base 134 of the leaflet frame 130; wherein the second film 162 defines a leaflet 140. Each leaflet 140 defines a leaflet free edge 142.

In accordance with an embodiment, the leaflet 140 can comprise a biocompatible material that is not of a biological source and that is sufficiently compliant and strong for the particular purpose, such as a biocompatible polymer. In an embodiment, the leaflet 140 comprises a membrane that is combined with an elastomer to form a composite material. In accordance with other embodiments, the biocompatible material that makes up the leaflet 140 comprises a biological material, such as, but not limited to, bovine pericardium.

The shape of the leaflets 140 are defined in part by the shape of the leaflet frame 130 and the leaflet free edge 142. The shape of the leaflets 140 can also be defined by the structures and processes used to manufacture the valve 100, such as, but not limited, those described below. For example, in accordance with an embodiment, the shape of the leaflets 140 also depends in part on molding the leaflets 140 using molding and trimming processes to impart a predetermined shape to the leaflet 140.

In an embodiment, substantially the entire leaflet frame 130 lies adjacent to the body frame inner surface 129. As such, when the leaflets 140 are in a fully open position, the valve 100 presents a substantially circular valve orifice 102 as shown in FIG. 1C, where the leaflet frame 130 minimally extends into the valve orifice 102. Fluid flow is permitted through the valve orifice 102 when the leaflets 140 are in an open position.

The leaflets 140 generally flex about the base 134 of the U-shaped portion 132 as the leaflets 140 open and close. In an embodiment, when the valve 100 is closed, generally about half of each leaflet free edge 142 abuts an adjacent half of a leaflet free edge 142 of an adjacent leaflet 140, as shown in FIG. 1D. The three leaflets 140 of the embodiment of FIG. 1D meet at a triple point 148. The valve orifice 102 is occluded when the leaflets 140 are in the closed position stopping fluid flow.

The leaflet 140 can be configured to actuate at a pressure differential in the blood caused, for example, by the contraction of a ventricle or atrium of the heart, such pressure differential typically resulting from a fluid pressure building up on one side of the valve 100 when closed. As the pressure on an inflow side of the valve 100 rises above the pressure on the outflow side of the valve 100, the leaflet 140 opens and blood flows therethrough. As blood flows through the valve 100 into a neighboring chamber or blood vessel, the pressure equalizes. As the pressure on the outflow side of the valve 100 rises above the blood pressure on the inflow side of the valve 100, the leaflet 140 returns to the closed position generally preventing the retrograde flow of blood through the inflow side of the valve 100.

It is understood that the leaflet frame 130 can comprise any number of U-shaped portions 132, and thus leaflets 140, suitable for a particular purpose. Leaflet frames 130 comprising one, two, three or more U-shaped portions 132 and corresponding leaflets 140 are contemplated.

Valve Film

As shown in FIG. 1A, the body frame 120 is located coaxially about the leaflet frame 130 and, as shown in FIG. 2A, layered therewith in the unwrapped view of the valve 100. The valve 100 can comprise a film that couples at least a portion of the leaflet frame 130 to the body frame 120.

It is contemplated that the film 160 can be coupled to the leaflet frame 130 and the body frame 120 in many ways suitable for a particular purpose. By way of example, and not limited thereto, the body frame 120 can be wrapped with overlapping layers of a first film 161 having a first composition. The leaflet frame 130 can be wrapped with overlapping layers of a second film 162 having a second composition.

The film 160 can be coupled to the inside or outside surface of the leaflet frame 130 and body frame 120. In an embodiment, the film 160 can be coupled to both the inside and outside surfaces of both the leaflet frame 130 and the body frame 120. In another embodiment, the film 160 can be coupled to the inside surface of the leaflet frame 130 and the outside surface of the body frame 120 sandwiching at least a portion of the leaflet frame 130 and body frame 120 between the film 160, or vise versa, such that the leaflet frame 130 and body frame 120 are coupled together by the film 160.

The film 160 can be configured to prevent blood from traveling through or across the valve 100 other than through the valve orifice 102 when the leaflets 140 are in an open position. As such, the film 160 creates a barrier to blood flow in any interstitial space(s) of the body frame 120 and leaflet frame 130, and therebetween, that the film 160 covers.

The film 160 is fixedly secured or otherwise coupled at a single or a plurality of locations of the inside or outside surface of the body frame 120 and leaflet frame 130, for example, using one or more of taping, heat shrinking, adhesion and other processes known in the art. In some embodiments, a plurality of membrane/composite layers, i.e., a laminate, are used and can be coupled to the body frame 120 and the leaflet frame 130 to form at least a portion of the film 160.

The film 160 comprises any material(s) that have the suitable physical and mechanical properties to perform the functions described herein. A first film 161 coupled to the body frame 120 may comprise the same material that a second film 162 that the leaflet 140 comprises, as described above, or a different material. Similarly, the film 160 may or may not be homogenous in material composition. Different portions of the film 160 can comprise different materials which can give it predetermined physical and mechanical properties.

Leaflet Frame Engagement and Clasp

In accordance with an embodiment, any portion of the leaflet frame 130 that is not coupled to the body frame 120 by the film 160 can be in urging engagement against the body frame inner surface 129. In accordance with an embodiment, the leaflet frame 130 can have a spring bias wherein the leaflet frame 130 engages the body frame 120 in biased urging engagement.

In accordance with an embodiment, the posts 131 abut the inner surface 129 of the body frame 120, as shown in FIG. 1A. In accordance with yet another embodiment, the posts 131 are coupled with the body frame inner surface 129 by an engagement element (not shown) defined by the body frame 120.

In accordance with an embodiment, as shown in FIGS. 1A and 3A-3B, the posts 131 are positioned relative to the body frame 120 by the engagement of the posts 131 lying within a valley 128 defined by the body frame 120, as shown in FIG. 2A. The valley 128 can be operable to align the post 131 with the apex of the valley 128 so as to preferentially position the post 131 with respect to the body frame 120. It is understood that the posts 131 can lie entirely within the body frame 120, or at least partially extending from and outside of the body frame 120.

The engagement of the posts 131 of the leaflet frame 130 with the body frame 120 can provide support to the leaflet frame 130. The engagement of the posts 131 with the body frame 120 allows for the transfer of loading on the leaflet 140 to the leaflet frame 130 and then to the body frame 120. It is contemplated that the degree of engagement of the leaflet frame 130 with the body frame 120 will determine the degree of support provided on the leaflet frame 130 by the body frame 120, which can be predetermined for a particular purpose.

In other embodiments, a portion of the leaflet frame including a portion of the posts 131 is not coupled to the first film 160 and not held in engagement with the body frame inner surface 129 so as to allow inward flexing of the posts 131 under the loading of the leaflet 140 during valve operation, particularly when closing or closed. Flexing of the posts 131 can ensure that the leaflet free edges 142 coapt to form a tight seal when closed. In various embodiments, the degree of inward flexing of the posts 131 during valve operation will determine the degree of coaptation, which can be predetermined for a particular purpose.

In accordance with an embodiment, one or more clasps (not shown) or some other similar engagement mechanism can secure the post 131 to the body frame 120 and add a predetermined amount of structural rigidity to the leaflet frame 130. As such, loading on the leaflet frame 130 can at least partially be transferred or distributed to the body frame 120. In this regard, the clasp comprises any structure configured to interlock, connect, fasten, or otherwise hold the leaflet frame 130 and body frame 120 together. The clasp connecting the leaflet frame 130 to the body frame 120 is operable to transfer at least some of the load on the leaflet frame 130 to the body frame 120.

Body Frame and Leaflet Frame Compared

In embodiments of the valve 100, the inclusion of a body frame 120 and a leaflet frame 130 provides a means for providing different physical properties for each of the body frame 120 and the leaflet frame 130 suitable for a particular purpose. In accordance with an embodiment, the body frame 120 is less stiff as compared with the leaflet frame 130. The body frame 120, when engaged to the implant site, such as, but not limited to the tissue orifice 150 as shown in FIG. 4, is rigid enough to not significantly recoil to a smaller diameter or deform under physiological loading.

The physical properties of the body frame 120 and the leaflet frame 130 depends, in part, on the size, shape, thickness, material property of the body frame 120 and the leaflet frame 130 as well as the different physical properties and number of layers or wrappings of the film 160 as well as the coupling of the body frame 120 and the leaflet frame 130.

Film

The second film 162 that makes up the leaflet 140 can comprise any biocompatible material sufficiently compliant and flexible, such as a biocompatible polymer. The second film 162 can comprise a membrane that is combined with an elastomer to form a composite material. The second film 162, according to an embodiment, includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore, in accordance with an embodiment. The fibrils extend from the nodes in a plurality of directions, and the membrane has a generally homogeneous structure. Membranes having this microstructure can typically exhibit a ratio of matrix tensile strength in two orthogonal directions of less than 2, and possibly less than 1.5. Embodiments of expanded fluoropolymer membrane provided herein contain a majority of fibrils having a diameter that is less than about 1 µm. Other embodiments of expanded fluoropolymer membrane provided herein contain a majority of fibrils having a diameter that is less than 0.1 µm. The embodiments provided herein recognize that a membrane comprising fibrils the majority of which are less than about 1 to beyond less than about 0.1 µm provide a significant improvement to, at least, but not limited to, the durability and lifetime of the heart valve when used as leaflet material. Embodiments of expanded fluoropolymer membrane provided herein may have a mean flow pore sizes of less than about 5 µm, less than about 1 µm, and less than about 0.10 µm, in accordance with embodiments.

In another embodiment, the expanded fluoropolymer membrane has a microstructure of substantially only fibrils, such as, for example, as is generally taught by U.S. Pat. No. 7,306,729, to Bacino, in accordance with an embodiment. The expanded fluoropolymer membrane having substantially only fibrils can possess a high surface area, such as greater than 20 m$^2$/g, or greater than 25 m$^2$/g, and in some embodiments can provide a highly balanced strength material having a product of matrix tensile strengths in two orthogonal directions of at least 1.5×10$^5$ MPa$^2$, and/or a ratio of matrix tensile strengths in two orthogonal directions of less than 4, and possibly less than 1.5. Embodiments of expanded fluoropolymer membrane provided herein contain a majority of fibrils having a diameter that is less than about 1 µm. Other embodiments of expanded fluoropolymer membrane provided herein contain a majority of fibrils having a diameter that is less than about 0.1 µm. The embodiments provided herein recognize that a membrane comprising fibrils the majority of which are less than about 1 to beyond less than about 0.1 µm provide a significant improvement to, at least, but not limited to, the durability and lifetime of the heart valve when used as leaflet material. Embodiments of expanded fluoropolymer membrane provided herein may have a mean flow pore sizes of less than about 5 µm, less than about 1 µm, and less than about 0.10 µm, in accordance with embodiments.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 µm. The expanded fluoropolymer membrane can possess a mass per area of about 1.15 g/m$^2$. Membranes according to an embodiment of the invention can have matrix tensile strengths of about 411 MPa in the longitudinal direction and 315 MPa in the transverse direction.

Additional materials can be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 μm and a mass per area of about 4.1 g/m².

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet 140 by eliminating or reducing the stiffening observed with ePTFE-only materials. In addition, it can reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment, the elastomer is present in substantially all of the pores of the at least one fluoropolymer layer. Having elastomer filling the pore volume or present in substantially all of the pores reduces the space in which foreign materials can be undesirably incorporated into the composite material. An example of such foreign material is calcium that can be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. hereby incorporated by reference in its entirety. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In another embodiment, the ePTFE comprises pores with the elastomer present in substantially all of the pores. The composite material comprises less than about 80% ePTFE by weight in the range of about 10% to 90%.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang hereby incorporated by reference in its entirety.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones(organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Sewing Cuff

The valve 100 further comprises a sewing cuff 170 about a body frame outer surface 127 in accordance with an embodiment, as shown in FIG. 1B; not shown in FIG. 1A for clarity. The sewing cuff 170 is operable to provide structure that receives suture for coupling to the implant site. The sewing cuff 170 may comprise any suitable material, such as, but not limited to, double velour polyester. The sewing cuff 170 may be located circumferentially around the base frame 120 or perivalvular depending from the base frame 120.

Other Considerations

In accordance with an embodiment, the valve 100 can be configured to prevent interference with a heart conduction system by not covering a bundle branch in the left ventricle when implanted, such as might be encountered with an aortic valve replacement procedure. For example, the valve 100 can comprise a length of less than about 25 mm or less than about 18 mm. The valve 100 can also comprise an aspect ratio of less than one, wherein the ratio describes the relationship between the length of the valve 100 to the functional diameter. However, the valve 100 can be constructed at any length and, more generally, any desirable dimension.

The valve 100 can further comprise a bio-active agent. Bio-active agents can be coated onto a portion or the entirety of the film 160 for controlled release of the agents once the valve 100 is implanted. The bio-active agents can include, but are not limited to, vasodilator, anti-coagulants, anti-platelet, anti-thrombogenic agents, such as, but not limited to, heparin. Other bio-active agents can also include, but are not limited to agents such as, but not limited to, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Method of Making

Figure 5:
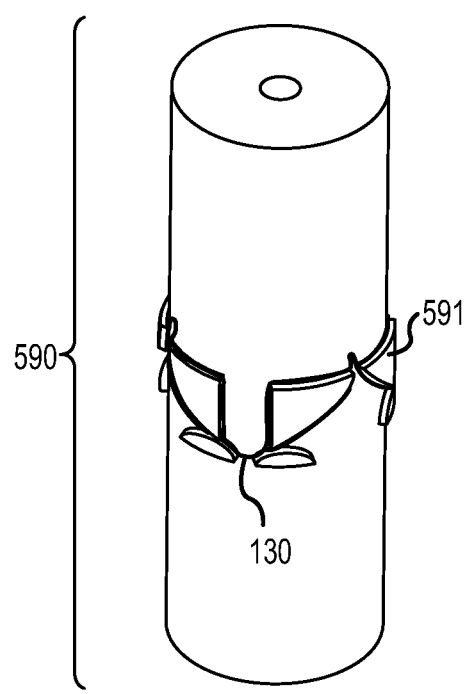
FIG. 5 is a perspective view of an embodiment of a winding jig for forming a wire into a leaflet frame.

Embodiments described herein also pertain to a method of making the valve embodiments as described herein. In order to make the various embodiments, a winding jig and a two-piece leaflet mandrel can be used. With reference to FIG. 5, winding jig 590 comprises a structural form defining the valve orifice of the valve and a leaflet frame guide 591 configured to facilitate the shaping of a wire into a desired shape of the leaflet frame 130.

With reference to FIG. 5, a method of making the leaflet frame 130 can comprise the step of shaping a wire to form leaflet frame 130. Winding jig 590 can be used to form the leaflet frame 130 wherein wire is bent around posts and guides and then heat set. The ends of the wire are coupled together.

Figure 6A:
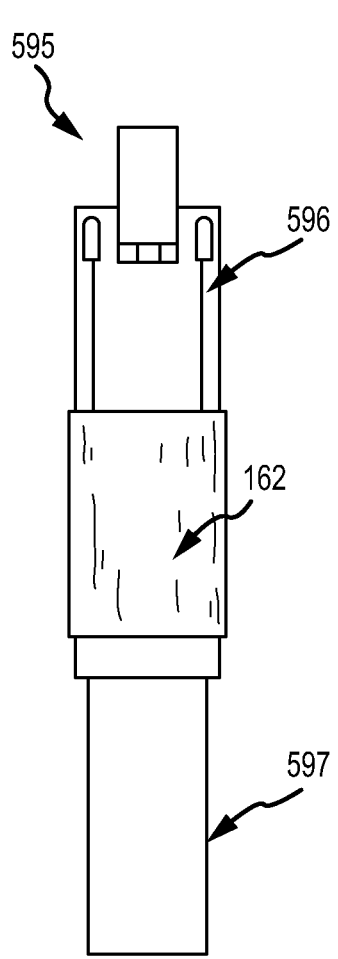
Figure 6B:
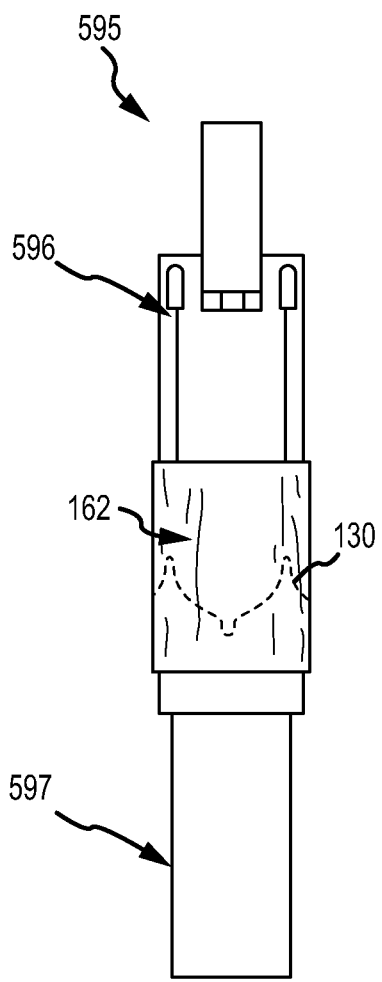
Figure 6H:
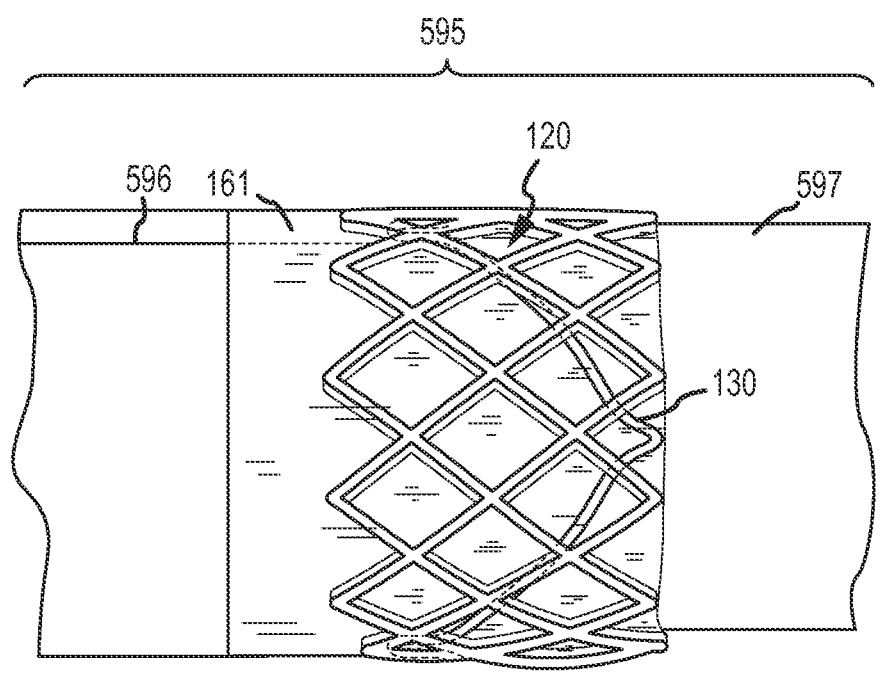

With reference to FIGS. 6A-6H, an embodiment of a method of making valve 100 comprises the steps of wrapping a first layer of second film 162, e.g., a composite as described herein, into a tubular form about a two-piece mandrel 597, as shown in FIG. 6A; placing the leaflet frame 130 over the first layer of second film 162; forming a second layer of second film 162 over the leaflet frame 130, as shown in FIG. 6B, placing a leaflet clamp 596 in urging engagement with the second film 162 about the U-shaped portions 132 of the leaflet frame 130 that will become the leaflets 140, as shown in FIG. 6C; molding the leaflets 140 with the leaflet clamp 596, as shown in FIG. 6D-6E; forming a third layer comprising a first film 161 over the leaflet frame 130, as shown in FIG. 6F; placing the body frame 120 about the third layer and the leaflet frame 130, as shown in FIG. 6G; wrapping a fourth layer comprising the first film 161 over the body frame 120, as shown in FIG. 6H; and thermally setting the assembly.

With reference to FIG. 6E, a two-piece mandrel 595 comprises a leaflet clamp 596 and a base mold 597 which together form the mandrel to mold a tubular membrane or composite to form the leaflets 140. Leaflet clamp 596 can comprise contoured grooves 594 along the seams of the leaflet clamp 596 wherein the posts 131 will be placed into in order to facilitate the desired spring bias or inward flexing in the leaflet frame 130.

EXAMPLE

By way of example, one embodiment of a valve was made as follows:

A leaflet frame was constructed by winding a nitinol wire (0.020" diameter) onto a winding jig as illustrated in FIG. 5. Once the pattern as shown in FIG. 2B was obtained, the frame was shape set in an oven set to 450° C. for 10 minutes. The two ends of the wire were coupled together. The leaflet frame was then exposed to a surface roughening step to improve adherence of the second film 162 to the leaflet frame. The leaflet frame was submersed in an ultrasonic bath of acetone for approximately five minutes. The leaflet frame surface was then subjected to a plasma treatment with methods commonly known to those having ordinary skill in the art.

FEP powder (Daikin America, Orangeburg N.Y.) was applied to the leaflet frame. The leaflet frame was then heated in a forced air oven set to 320° C. for approximately three minutes. In this way, the powder was melted and adhered as a thin coating to the entire frame. The leaflet frame was removed from the oven and left to cool to room temperature.

A body frame was laser cut from a tube of 316 stainless steel having a wall thickness of about 0.5 mm (0.02"), a diameter of about 2.5 cm (1.0"), and a length of 2 cm. A diamond-shaped pattern was cut into the tube to form an annular-shaped body frame as shown in FIG. 2B. The same surface treatment and FEP powder coating steps as described above were applied to the body frame.

A second film 162 was obtained. A membrane of ePTFE can be manufactured according to the general teachings described in U.S. Pat. No. 7,306,729 to Bacino et al. The ePTFE membrane can have a mass per area of 1.15 g/m$^2$, a bubble point of 79.7 MPa, a thickness of about 1.016 µm, a matrix tensile strength of 410.9 MPa in the longitudinal direction and 315.4 MPa in the transverse direction. The ePTFE membrane was imbibed with a fluoroelastomer to form a composite material.

A fluoroelastomer that is a copolymer comprising tetrafluoroethylene and perfluoro(methyl vinylether) as described in U.S. Pat. No. 7,462,675 to Chang, et al. was obtained. The copolymer consists essentially of between about 65 and 70 weight percent perfluoromethyl vinyl ether and complementally about 35 and 30 weight percent tetrafluoroethylene.

This copolymer was dissolved in Novec HFE7500 (3M, St Paul, Minn.) in a 2.5% concentration. The ePTFE membrane (while being supported by a polypropylene release film) was coated with the prepared solution using a mayer bar and dried in a convection oven set to 145° C. for 30 seconds thereby creating an imbibed composite material. After the two coating steps, the final ePTFE/fluoroelastomer or composite material had a mass per area of approximately 4.08 g/m², 28.22% fluoropolymer by weight, a dome burst strength of 15.9 KPa, and a thickness of 1.89 µm.

Fifteen layers of the composite material, the second film 162, were wrapped around the combined 25 mm diameter aluminum mandrel assembly shown in FIG. 6A with the elastomer rich side facing away from the mandrel. The layers of composite material were each circumferentially wrapped around the mandrel so as to orient the transverse direction of the composite along the longitudinal axis of the mandrel. Each additional layer wrapped around the mandrel assembly was oriented in the same fashion.

The leaflet frame was everted from its wire wound condition, then coaxially positioned on the mandrel, as illustrated in FIG. 6B.

A second layer of the second film 162 comprising five additional layers of membrane material were wrapped around the combined mandrel assembly and over the leaflet frame with the elastomer rich side facing toward the leaflet frame The leaflets were then formed to a predetermined shape by positioning the leaflet clamp 596 as shown in FIGS. 6C-6E and subsequently closing the leaflet clamp 596 against the second film 162 about the about the U-shaped portions 132 of the leaflet frame 130 that subsequently became the leaflets 140.

A first layer comprising first film 161 comprising five layers of membrane material were wrapped around the combined mandrel assembly with the elastomer rich side facing outward, as shown in FIG. 6F. The body frame was then positioned onto the mandrel in operable relationship to the leaflet frame, as shown in FIG. 6G. A second layer comprising the first film 161 comprising five additional layers of composite material were wrapped around the body frame with the elastomer rich side of each layer facing toward the body frame, as shown in FIG. 6G.

The combined mandrel assembly was then thermal treated to set the leaflet shape and to consolidate the biocompatible material. The first film 161 and second film 162 were trimmed in accordance with the configuration as shown in FIGS. 1A-2B.

Testing Methods

It should be understood that although certain methods and equipment are described below, any method or equipment determined suitable by one of ordinary skill in the art may be alternatively utilized.

Bubble Point And Mean Flow Pore Size

Bubble point and mean flow pore size were measured according to the general teachings of ASTM F31 6-03 using a capillary flow Porometer, Model CFP 1500AEXL from Porous Materials, Inc., Ithaca N.Y., USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. The test fluid was isopropyl alcohol. Using the Capwin software version 7.73.012 the following parameters were set as specified in the table below. As used herein, mean flow pore size and pore size are used interchangeably.

| Parameter | Set Point |
|---|---|
| Maxflow (cm³/m) | 200000 |
| Bublflow (cm³/m) | 100 |

-continued

| Parameter | Set Point |
|---|---|
| F/PT (old bubltime) | 50 |
| Minbpress (PSI) | 0 |
| Zerotime (sec) | 1 |
| V2incr (cts) | 10 |
| Preginc (cts) | 1 |
| Pulse delay (sec) | 2 |
| Maxpre (PSI) | 500 |
| Pulse width (sec) | 0.2 |
| Mineqtime (sec) | 30 |
| Presslew (cts) | 10 |
| Flowslew (cts) | 50 |
| Eqiter | 3 |
| Aveiter | 20 |
| Maxpdif (PSI) | 0.1 |
| Maxfdif (PSI) | 50 |
| Sartp (PSI) | 1 |
| Sartf (cm³/m) | 500 |

Presence of Elastomer within the Pores

The presence of elastomer within the pores can be determined by several methods known to those having ordinary skill in the art, such as surface and/or cross section visual, or other analyses. These analyses can be performed prior to and after the removal of elastomer from the composite.

Diameter of Fibrils

The average diameter of the fibrils was estimated by examining micrographs that were obtained having at a magnification suitable for showing numerous fibrils. In the case of a composite material, it may be necessary to extract the elastomer or other material that may be filling the pores, by any suitable means, to expose the fibrils.

Mass, Thickness, and Density of ePTFE Membranes

Membrane thickness was measured by placing the membrane between the two plates of a Käfer FZ1000/30 thickness snap gauge Käfer Messuhrenfabrik GmbH, Villingen-Schwenningen, Germany. The average of the three measurements was reported.

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho=m/(w*l*l)$, in which: $\rho$=density (g/cm³), m=mass (g), w=width (cm), l=length (cm), and t=thickness (cm). The average of three measurements was reported.

Matrix Tensile Strength (MTS) of ePTFE Membranes

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the Käfer FZ1000/30 snap gauge; alternatively, any suitable means for measuring thickness may be used. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), where the bulk density of the PTFE was taken to be about 2.2 g/cm$^3$.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed:

1. A valve comprising:
   a leaflet frame having a generally annular shape having an outer surface and defining a leaflet frame lumen and a plurality of U-shaped portions each defining a base and a plurality of posts;
   a body frame having a generally tubular shape and having an inner surface defining a body frame lumen, the leaflet frame being located coaxial with the body frame lumen with at least a portion of the leaflet frame positioned within the body frame lumen at a longitudinally fixed position relative to the body frame;
   a first film including a plurality of layers sandwiching the leaflet frame such that the first film is coupled to the leaflet frame, the first film defining a plurality of leaflets, each leaflet of the plurality of leaflets having a leaflet free edge, being operable to abut adjacent leaflet free edges, and being moveable between an open and closed position, the first film having an inner surface facing toward the leaflet frame lumen and an outer surface facing away from the leaflet frame lumen; and
   a second film including a plurality of layers sandwiching the body frame such that the second film is coupled to the body frame, the second film having an inner surface facing toward the body frame lumen and an outer surface facing away from the body frame lumen;
   the second film being bonded to the first film to form a laminate such that the outer surface of the leaflet frame is bonded to the inner surface of the body frame by the first and second films and such that the leaflet frame is secured within the body frame lumen by the laminated first and second films at the longitudinally fixed position.

2. The valve of claim 1, wherein the body frame is stiffer than the leaflet frame.

3. The valve of claim 1, wherein at least one of the first and second films comprises a laminate having more than one fluoropolymer layer.

4. The valve of claim 1, wherein at least one of the first and second films comprises a laminate having more than one expanded fluoropolymer layer.

5. The valve of claim 1, wherein at least one of the first and second films is imbibed with an elastomer.

6. The valve of claim 5, wherein the elastomer comprises perfluoromethyl vinyl ether and tetrafluoroethylene.

7. The valve of claim 1, wherein at least one of the first and second films comprises a laminate having more than one ePTFE layer.

8. The valve of claim 1, wherein the leaflet frame comprises a shape-memory material.

9. The valve of claim 1, wherein the leaflet frame comprises a metallic material.

10. The valve of claim 1, wherein,
    the first film comprises a first composite material having at least one fluoropolymer membrane layer defining the plurality of pores of the first film, and
    the second film comprises a second composite material having at least one fluoropolymer membrane defining the plurality of pores of the second film.

11. The valve of claim 10, wherein each of the first and second composite materials each comprise fluoropolymer membrane by weight in a range of about 10% to 90%.

12. The valve of claim 10, wherein each of the first and second films comprises a copolymer of tetrafluoroethylene and perfluoromethyl vinyl ether.

13. The valve of claim 10, wherein at least one of the fluoropolymer membranes of each of the first and second composite materials comprises ePTFE.

14. The valve of claim 1, wherein the first and second films are the same type of material.

15. A valve comprising:
    a leaflet frame having a generally annular shape and an inner surface defining a leaflet frame lumen and a plurality of U-shaped portions each defining a base and a plurality of posts;
    a body frame having a generally tubular shape, an outer surface, and an inner surface defining a body frame lumen, the leaflet frame being located coaxial with the body frame lumen with at least a portion of the leaflet frame longitudinally fixed within the body frame lumen;
    a first film having an outer surface coupled to the inner surface of the leaflet frame and defining a plurality of leaflets, each leaflet of the plurality of leaflets having a leaflet free edge, being operable to abut adjacent leaflet free edges, and being moveable between an open and closed position;
    a second film coupled to the outer surface of the body frame, the second film having an inner surface coupled to the outer surface of the body frame; and
    the second film overwrapping the first film and consolidated with the first film such that the outer surface of the leaflet frame is bonded to the inner surface of the body frame and maintained at the longitudinally fixed position by the laminate formed by the first and second films.

16. The valve of claim 15, wherein the leaflet frame has a spring bias wherein the leaflet frame engages the body frame in biased urging engagement.

17. The valve of claim 15, wherein the plurality of posts abut the inner surface of the body frame.

18. The valve of claim 15, wherein the plurality of posts are coupled with the inner surface of the body frame.

19. The valve of claim 15, wherein the plurality of posts abut the inner surface of the body frame.

20. A valve comprising:
    a leaflet frame having a generally annular shape and an inner surface defining a leaflet frame lumen and including a base and a plurality of posts extending from the base;
    a body frame having a generally tubular shape, an outer surface, and an inner surface defining a body frame lumen, the leaflet frame being located coaxial with the body frame lumen with at least a portion of the leaflet frame positioned within the body frame lumen at a longitudinally fixed position within the body frame lumen, wherein the leaflet frame and the body frame are engaged together in biased, urging engagement; and a plurality of film layers forming a laminate sandwiching the leaflet frame and the body frame to bond the leaflet frame within the body frame at the longitudinally fixed position, the plurality of film layers defining a plurality of leaflets each having a base coupled to the leaflet frame and a free edge operable to abut adjacent leaflet free edges and being moveable between an open and closed position.

* * * * *